(12) United States Patent
Nilsson et al.

(10) Patent No.: US 7,766,945 B2
(45) Date of Patent: Aug. 3, 2010

(54) SCREW AND ROD FIXATION SYSTEM

(75) Inventors: C. Michael Nilsson, Cleveland Heights, OH (US); Terrance M. Stahurski, Seven Hills, OH (US); Jeffrey Thramann, Longmont, CO (US); Michael Fulton, Superior, CO (US)

(73) Assignee: Lanx, Inc., Broomfield, CO (US)

( * ) Notice: Subject to any disclaimer, the term of this patent is extended or adjusted under 35 U.S.C. 154(b) by 1155 days.

(21) Appl. No.: 10/915,902

(22) Filed: Aug. 10, 2004

(65) Prior Publication Data

US 2006/0036242 A1 Feb. 16, 2006

(51) Int. Cl.
*A61B 17/70* (2006.01)
(52) U.S. Cl. ............................................ 606/266
(58) Field of Classification Search ............. 606/61, 606/300, 301, 305–308, 246, 264–270, 272, 606/278; 403/52, 74, 83, 90, 122; 411/393
See application file for complete search history.

(56) References Cited

U.S. PATENT DOCUMENTS

| | | | |
|---|---|---|---|
| 4,569,338 A | 2/1986 | Edwards | |
| 4,887,596 A | 12/1989 | Sherman | |
| 4,946,458 A | 8/1990 | Harms et al. | |
| 5,067,955 A | 11/1991 | Cotrel | |
| 5,120,171 A | 6/1992 | Lasner | |
| 5,190,543 A | 3/1993 | Schläpfer | |
| 5,207,678 A | 5/1993 | Harms et al. | |
| 5,226,766 A | 7/1993 | Lasner | |
| 5,312,404 A | 5/1994 | Asher et al. | |
| 5,395,371 A | 3/1995 | Miller et al. | |
| 5,417,533 A | 5/1995 | Lasner | |
| 5,466,237 A | 11/1995 | Byrd, III et al. | |
| 5,474,555 A | 12/1995 | Puno et al. | |
| 5,486,174 A | 1/1996 | Fournet-Fayard et al. | |
| 5,492,442 A | 2/1996 | Lasner | |
| 5,499,983 A | 3/1996 | Hughes | |
| 5,505,731 A | 4/1996 | Tornier | |
| 5,520,689 A | 5/1996 | Schläpfer et al. | |
| 5,531,746 A | 7/1996 | Errico et al. | |

(Continued)

FOREIGN PATENT DOCUMENTS

EP 1 354 563 10/2003

(Continued)

OTHER PUBLICATIONS

Notification of Transmittal of the International Search Report and the Written Opinion of the International Searching Authority, of the Declaration from the International Bureau, Oct. 10, 2008.

(Continued)

*Primary Examiner*—Eduardo C Robert
*Assistant Examiner*—David Comstock
(74) *Attorney, Agent, or Firm*—Holland & Hart LLP (57) ABSTRACT

The present invention provides a stabile construct to facilitate connecting a spinal fixation rod to a plurality of vertebral bodies. The construct or implant comprises a housing and an insert. The housing and insert are shaped to cooperatively engage the bone screw and rod to provide a stable construct that allows for polyaxial orientation between the bone screw and the remainder of the construct.

37 Claims, 8 Drawing Sheets

U.S. PATENT DOCUMENTS

| | | | |
|---|---|---|---|
| 5,536,268 A | 7/1996 | Griss | |
| 5,540,690 A | 7/1996 | Miller et al. | |
| 5,549,608 A | 8/1996 | Errico et al. | |
| 5,554,157 A | 9/1996 | Errico et al. | |
| 5,569,247 A | 10/1996 | Morrison | |
| 5,569,248 A | 10/1996 | Mathews | |
| 5,584,834 A | 12/1996 | Errico et al. | |
| 5,586,984 A | 12/1996 | Errico et al. | |
| 5,591,166 A | 1/1997 | Bernhardt et al. | |
| 5,609,592 A | 3/1997 | Brumfield et al. | |
| 5,628,740 A | 5/1997 | Mullane | |
| 5,634,925 A | 6/1997 | Urbanski | |
| 5,643,264 A | 7/1997 | Sherman et al. | |
| 5,647,873 A | 7/1997 | Errico et al. | |
| 5,653,708 A | 8/1997 | Howland | |
| 5,662,653 A | 9/1997 | Songer et al. | |
| 5,669,911 A | 9/1997 | Errico et al. | |
| 5,672,176 A | 9/1997 | Biedermann et al. | |
| 5,683,390 A | 11/1997 | Metz-Stavenhagen et al. | |
| 5,690,630 A | 11/1997 | Errico et al. | |
| 5,725,528 A | 3/1998 | Errico et al. | |
| 5,728,098 A | 3/1998 | Sherman et al. | |
| 5,733,286 A | 3/1998 | Errico et al. | |
| 5,735,851 A | 4/1998 | Errico et al. | |
| 5,738,685 A | 4/1998 | Halm et al. | |
| 5,752,957 A | 5/1998 | Ralph et al. | |
| 5,776,135 A | 7/1998 | Errico et al. | |
| 5,782,833 A | 7/1998 | Haider | |
| 5,785,711 A | 7/1998 | Errico et al. | |
| 5,810,819 A | 9/1998 | Errico et al. | |
| 5,814,046 A | 9/1998 | Hopf | |
| 5,817,094 A | 10/1998 | Errico et al. | |
| 5,863,293 A | 1/1999 | Richelsoph | |
| 5,879,350 A | 3/1999 | Sherman et al. | |
| 5,882,350 A | 3/1999 | Ralph et al. | |
| 5,891,145 A | 4/1999 | Morrison et al. | |
| 5,910,142 A | 6/1999 | Tatar | |
| 5,954,725 A | 9/1999 | Sherman et al. | |
| 5,961,518 A | 10/1999 | Errico et al. | |
| 5,964,760 A | 10/1999 | Richelsoph | |
| 5,989,254 A | 11/1999 | Katz | |
| 5,997,539 A | 12/1999 | Errico et al. | |
| 6,004,332 A | 12/1999 | Yoon et al. | |
| 6,017,344 A | 1/2000 | Errico et al. | |
| 6,053,917 A | 4/2000 | Sherman et al. | |
| 6,063,089 A | 5/2000 | Errico et al. | |
| 6,074,393 A | 6/2000 | Sitoto | |
| 6,090,111 A | 7/2000 | Nichols | |
| 6,113,601 A | 9/2000 | Tatar | |
| 6,132,434 A | 10/2000 | Sherman et al. | |
| 6,183,472 B1 | 2/2001 | Lutz | |
| 6,224,598 B1 | 5/2001 | Jackson | |
| 6,238,396 B1 | 5/2001 | Lombardo | |
| 6,241,731 B1 | 6/2001 | Fiz | |
| 6,287,311 B1 | 9/2001 | Sherman et al. | |
| 6,325,802 B1 | 12/2001 | Frigg | |
| 6,361,535 B2 | 3/2002 | Jackson | |
| RE37,665 E | 4/2002 | Ralph et al. | |
| 6,368,320 B1 | 4/2002 | Le Couedic et al. | |
| 6,368,321 B1 | 4/2002 | Jackson | |
| 6,402,752 B2 | 6/2002 | Schäffler-Wachter et al. | |
| 6,413,257 B1 | 7/2002 | Lin et al. | |
| 6,416,515 B1 | 7/2002 | Wagner | |
| 6,423,064 B1 | 7/2002 | Kluger | |
| 6,440,132 B1 | 8/2002 | Jackson | |
| 6,440,137 B1 | 8/2002 | Horvath et al. | |
| 6,451,021 B1 | 9/2002 | Ralph et al. | |
| 6,454,773 B1 | 9/2002 | Sherman et al. | |
| 6,478,798 B1 | 11/2002 | Howland | |
| 6,482,207 B1 | 11/2002 | Errico | |
| 6,485,494 B1 | 11/2002 | Haider | |
| 6,488,681 B2 | 12/2002 | Martin et al. | |
| 6,533,790 B1 | 3/2003 | Liu | |
| 6,540,748 B2 | 4/2003 | Lombardo | |
| 6,540,749 B2 | 4/2003 | Schäfer et al. | |
| 6,554,834 B1 | 4/2003 | Crozet et al. | |
| 6,562,040 B1 | 5/2003 | Wagner | |
| 6,565,566 B1 | 5/2003 | Wagner et al. | |
| 6,565,567 B1 | 5/2003 | Haider | |
| 6,585,740 B2 | 7/2003 | Schlapfer et al. | |
| 6,610,062 B2 | 8/2003 | Bailey et al. | |
| 6,613,050 B1 | 9/2003 | Wagner et al. | |
| 6,626,908 B2 | 9/2003 | Cooper et al. | |
| 6,896,677 B1 * | 5/2005 | Lin | 606/61 |
| 7,211,086 B2 * | 5/2007 | Biedermann | 606/61 |
| 2002/0010467 A1 * | 1/2002 | Cooper et al. | 606/61 |
| 2004/0143265 A1 | 7/2004 | Landry et al. | |
| 2005/0080415 A1 | 4/2005 | Keyer et al. | |
| 2005/0090821 A1 | 4/2005 | Berrevoets et al. | |
| 2005/0107789 A1 | 5/2005 | Sweeney | |
| 2005/0143823 A1 | 6/2005 | Boyd et al. | |
| 2005/0177154 A1 | 8/2005 | Moumene et al. | |
| 2005/0187548 A1 | 8/2005 | Butler et al. | |
| 2005/0192571 A1 | 9/2005 | Abdelgany | |
| 2005/0228377 A1 | 10/2005 | Chao et al. | |

FOREIGN PATENT DOCUMENTS

| WO | WO 01/97701 | 12/2001 |
|---|---|---|

OTHER PUBLICATIONS

Supplementary European Search Report Feb. 23, 2009.

* cited by examiner

SCREW AND ROD FIXATION SYSTEM

FIELD OF THE INVENTION

The present invention relates to spinal fixation devices and more particularly to a pedicle screw and rod fixation assembly useful in stabilizing a spine of a patient.

BACKGROUND OF THE INVENTION

Over the years, several techniques and systems have been developed for correcting spinal injuries and/or degenerative spinal processes. Spinal correction frequently requires stabilizing a portion of the spine to facilitate fusing portions of the spine or other correction methodologies. Medical correction of this type is frequently employed for many spinal conditions, such as, for example, degenerative disc disease, scoliosis, spinal stenosis, or the like. Frequently, these corrections also require the use of implants, such as, bone grafts. Stabilizing the spine allows bone growth between vertebral bodies such that a portion of the spine is fused into a solitary unit.

Several techniques and systems have been developed for correcting and stabilizing the spine and facilitating fusion at various levels of the spine. In one type of system, a rod is disposed longitudinally along the length of the spine in the region of concern. The rod is arranged according to the anatomy and the correction desired. In this system, the rod is aligned along the spine and engages various vertebrae along its length. The rod engages, or more typically the parallel rods engage, the spine using fixation elements, such as, anchors attached to vertebral bodies by a bone screw.

Anatomy and correction frequently require aligning the rod and screw at various angles along the length of the portion of correction. In order to provide this alignment, polyaxial screws/anchors have been developed. Many variations of polyaxial screw and rod fixation systems exist on the market today.

Despite the fact that numerous polyaxial rod fixation systems are on the market, improvement of the devices is desirable. Accordingly, there is a need for a screw and rod fixation system that provides a strong, effective, and secure lock of the screw and rod in the desired position and angle. Additionally, there is a need for a screw head securing mechanism or device that is minimal in size and has a reduced amount of components to provide for a simpler, more effective, and less cumbersome device for fixing screws.

SUMMARY OF THE INVENTION

To attain the advantages and in accordance with the purpose of the invention, as embodied and broadly described herein, a screw and rod fixation system is provided. The screw and rod fixation system comprises a bone screw having a threaded portion, a transition, and a head comprising a housing engaging surface and an insert engaging surface. The bone screw is provided in a housing with a bone facing surface and a top edge and a sidewall extending therebetween. A through hole extends from the top edge to the bone facing surface and a pair of opposing slots reside proximate the top edge. The housing has a screw head seating surface that is shaped to cooperatively engage the housing engaging surface to allow polyaxial orientation of the bone screw relative to a vertical axis of the housing. A housing couples to the bone screw and housing. The insert comprises a screw head engaging surface to cooperatively engage the insert engaging surface to allow polyaxial orientation of the bone screw relative to a vertical axis of the housing and an elongate rod rest shaped to seat a portion of the elongated rod, the elongated rod rest traversing the housing between the pair of opposing slots. An elongated rod traverses the housing between the pair of opposed slots and seated in the elongated rod rest.

The present invention further provides an insert useful in a device that couples spinal rods to vertebral bodies. The insert comprises a bone screw engaging surface and an elongated rest coupled to the bone screw engaging surface having an outer edge and a bottom surface opposite the elongated rest. A transition portion connects the bone screw engaging surface and the elongated rest. The insert cooperatively engage a bone screw to allow polyaxial orientation of the bone screw relative to the insert.

The foregoing and other features, utilities and advantages of the invention will be apparent from the following more particular description of a preferred embodiment of the invention as illustrated in the accompanying drawings.

BRIEF DESCRIPTION OF THE DRAWING

The accompanying drawings illustrate various embodiments of the present invention and are a part of the specification. The illustrated embodiments are merely examples and illustrations of the present invention and do not limit the scope of the invention.

DETAILED DESCRIPTION

Figure 1:
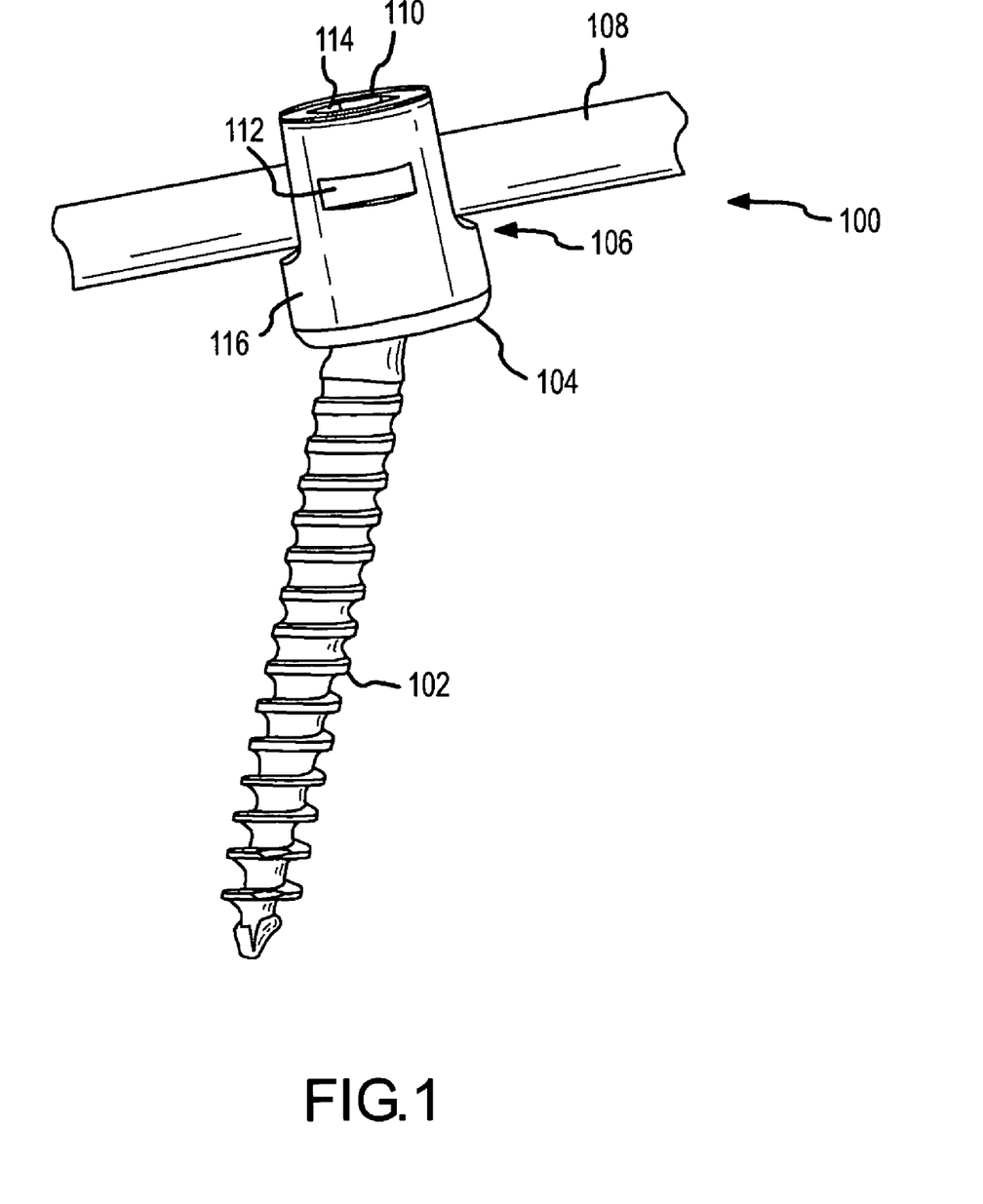
FIG. 1 shows a perspective view of a screw and rod fixation system in accordance with an embodiment of the present invention.
Figure 2:
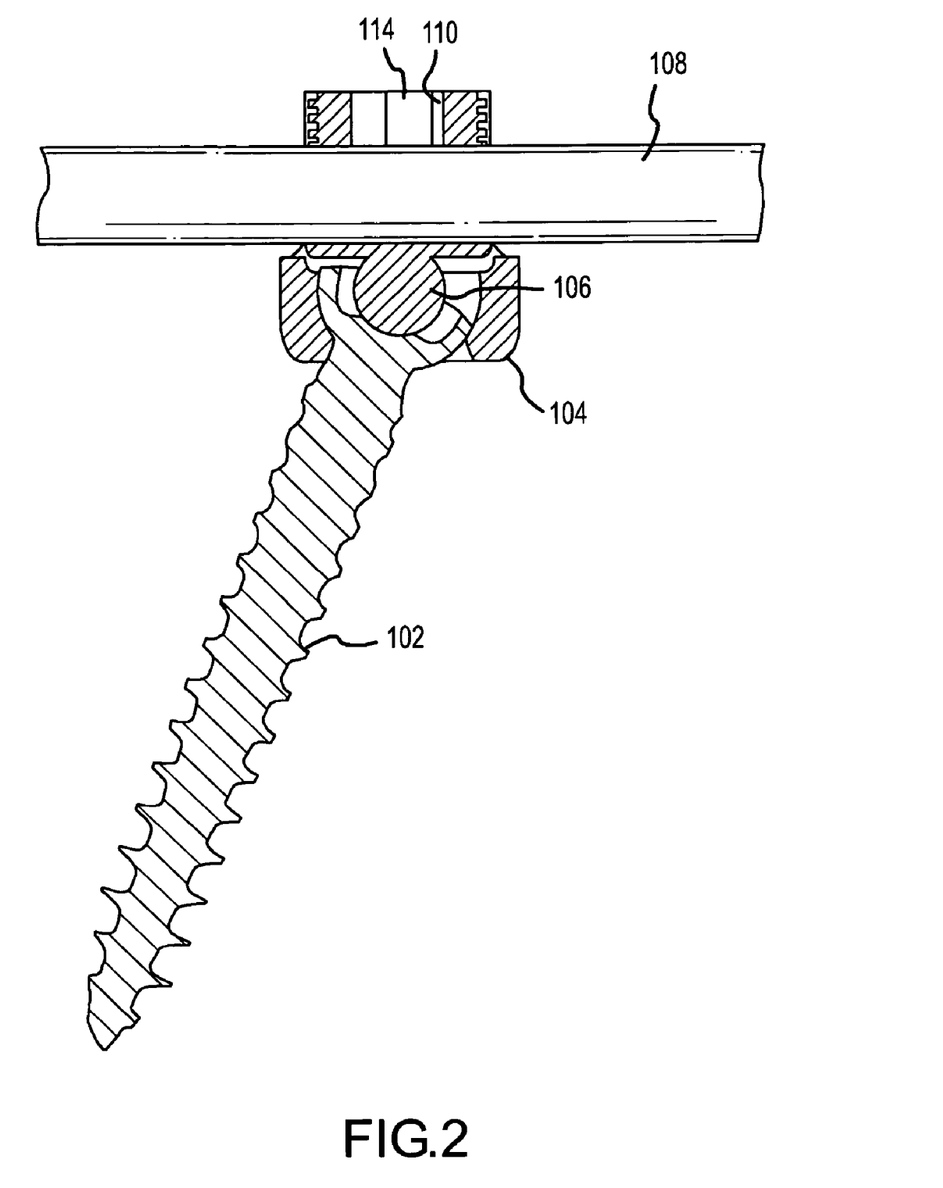
FIG. 2 shows a cross-sectional view of the system of FIG. 1.

Referring now to FIG. 1 and FIG. 2, and in accordance with certain embodiments of the present invention, a screw and rod fixation system 100 is shown. FIG. 1 shows a perspective view of system 100 while FIG. 2 shows a cross-sectional view of system 100. System 100 includes a bone screw 102, a housing 104, an insert 106, a rod 108, and a compressive member, such as, a setscrew 110. Housing 104 may contain one or more first mating surfaces 112. First mating surfaces 112 are designed to mate with a tool (not specifically shown). Also, setscrew 110 typically has one or more second mating surface 114 to mate with a tool (also not shown). As shown in FIG. 1, first mating surfaces 112 are actually slots on an outer surface 116 of housing 104. While shown as slots, first mating surfaces 112 may be any number of designs including one or more dimples, hex detents, or other equivalent mechanisms as are known in the art. Second mating surface 114 is shown with a hex shape to accept a hex driver useful in threading the setscrew. Of course, one of ordinary skill in the art would recognize other and equivalent first and second mating surfaces 112, 114 are possible.

Figure 3:
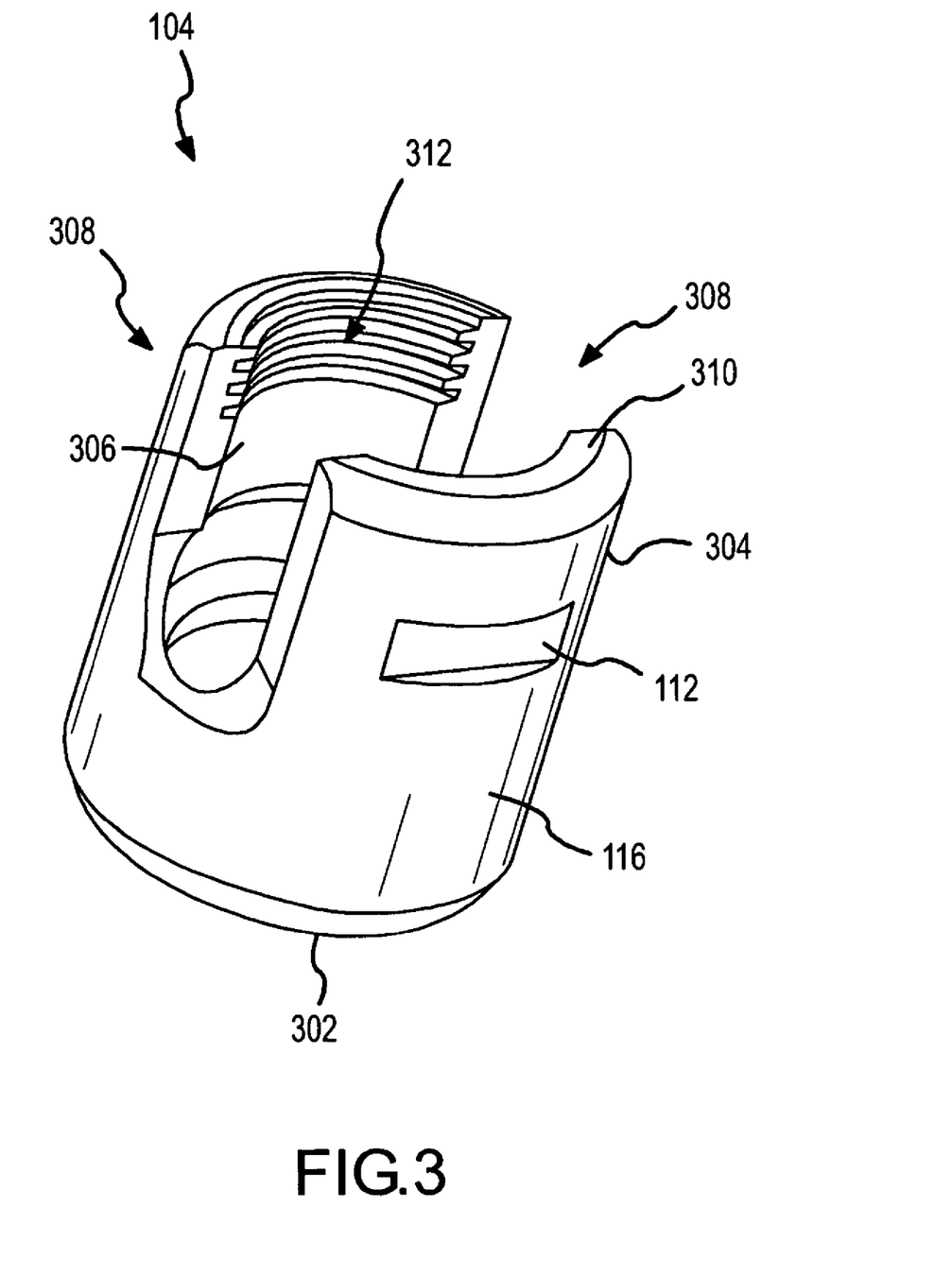
FIG. 3 shows a perspective view of a housing associated with an embodiment of the present invention shown in FIG. 1.
Figure 4:
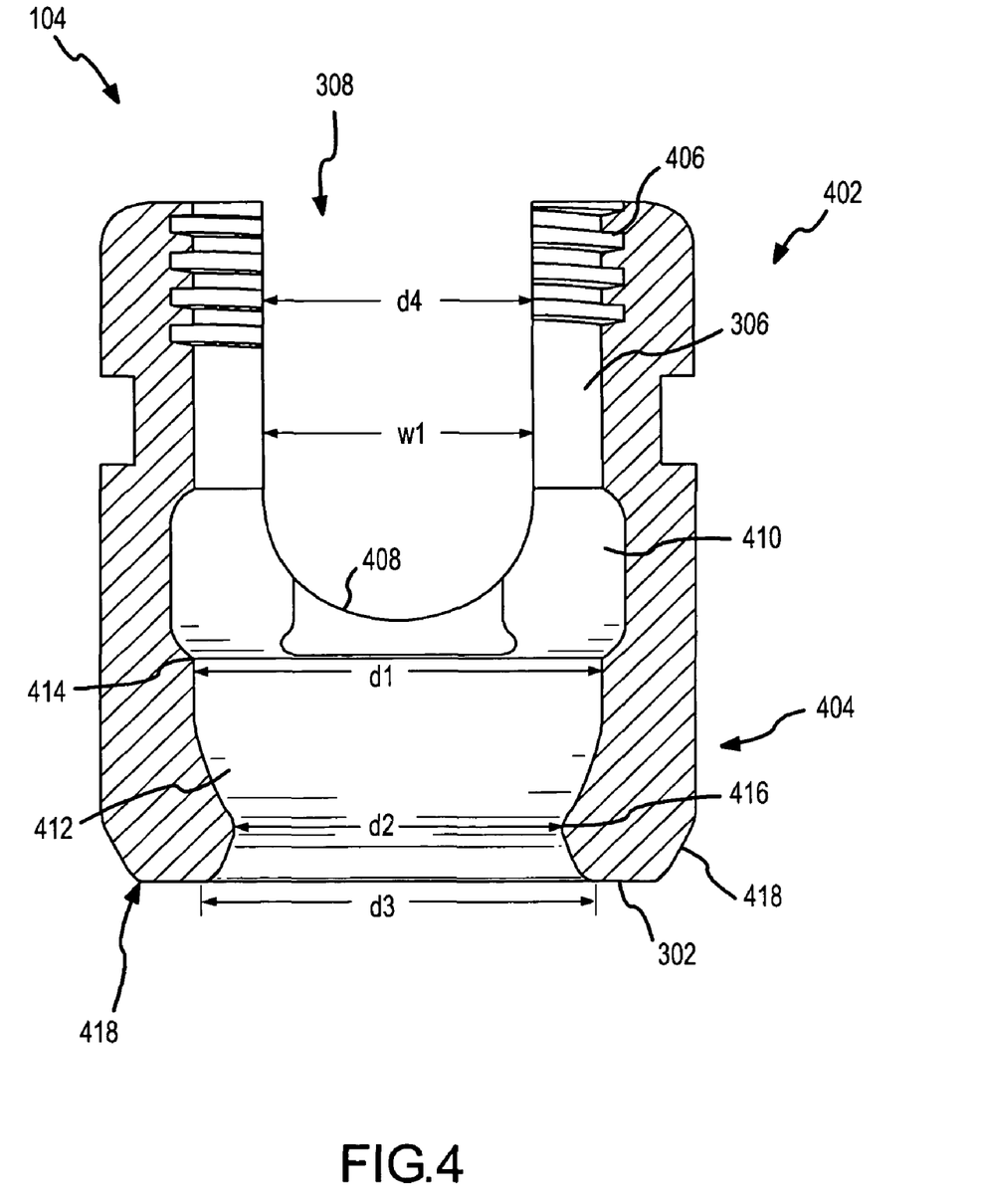
FIG. 4 shows a cross-sectional view of the housing of FIG. 3.

Referring now to FIGS. 3 and 4, housing 104 is described in more detail. Housing 104 may be referred to as a coupling device, seat, or anchor. Housing 104 has a bone facing surface 302, at least one sidewall 304 having an outer surface 116 and an inner surface 306 (best seen in FIG. 4), first mating surfaces 112, a pair of opposed slots 308 in sidewall 304, a top edge 310, and a through hole 312 extending from top edge 310, to bone facing surface 302. Housing 104 can be considered to have a rod receiving section 402 and a screw receiving section 404.

Notice, housing 104 is shown with one cylindrically shaped sidewall 304. It is believed providing housing 104 as a cylindrical shape reduces the profile of the device, but other shapes are possible, such as cubic or the like. If housing 104 had multiple sidewalls 304, the edges between the multiple sides should be beveled or rounded to inhibit tissue trauma.

Referring first to rod receiving section 402, inner surface 306 has first threads 406 extending partially along inner surface 306. As will be explained below, first threads 406 allow setscrew 110 to be threaded on housing 104. Slots 308 generally have a width W1 sufficiently wide to accept rod 108. Slots 308 have an insert seating surface 408, which will be explained further below. An insert groove 410 is provided about insert seating surface 408. Insert groove 410 allows provides a mechanism to lock and stabilize insert 106, as will be explained below.

As shown in FIG. 4, rod receiving section 402 provides a channel for a single rod 108 to traverse housing 104 from slot 308 to slot 308. In some instances, it may be difficult to provide a single rod 108 that can traverse the entire length of the spine necessitating multiple rods. Housing 104 could be easily converted to provide multiple rod guides. For example, housing 104 could have a second set of opposed slots substantially parallel to slots 308. Alternatively (but not shown), a rod cap/seat could be installed below threads 406 and above insert seating surface 408. The rod cap/seat would provide a cap side operatively sized and shaped to fit about rod 108 opposite the insert seating surface 408. The rod cap/seat provide a second seating surface operatively sized and shaped to fit about a second rod aligned substantially above rod 108. Setscrew 110 would provide compressive force to the substantially aligned rod, which would correspondingly provide compressive force to rod 108 and insert 106, etc.

Referring to screw receiving section 404, inner surface 306 has a screw head seating surface 412. Surface 412 has a shape corresponding to the screw head, described below. Surface 412 has an upper lip 414 and a lower lip 416. Upper lip 414 and lower lip 416 could comprise a beveled edge and/or protrusions. Upper lip 414, lower lip 416, and surface 412 cooperative engage the screw head to allow a polyaxial engagement of the screw 102, which will be described below. As shown, upper lip 414 has a first diameter d1 and lower lip 416 has a second diameter d2. First diameter d1 is larger than second diameter d2. Inner surface 306 terminates at bone facing surface 302. As shown, inner surface 306 flares out from second diameter d2 such that the bone side of through hole 312 has a third diameter d3 larger than second diameter d2, but generally smaller than first diameter d1. Outer surface 116 is generally perpendicular to top edge 310 and bone facing surface 302 to conserve space. As shown, bone facing surface 302 may have a rounded transition 418 between bone facing surface 302 and outer surface 116 to inhibit trauma to tissue. Also, top edge 310 has beveled or rounded edges.

Lastly, through hole 312 at top edge 310 has a fourth diameter d4. Diameter d4 is sufficiently large to accept the head of screw 102 and setscrew 110.

Figure 5:
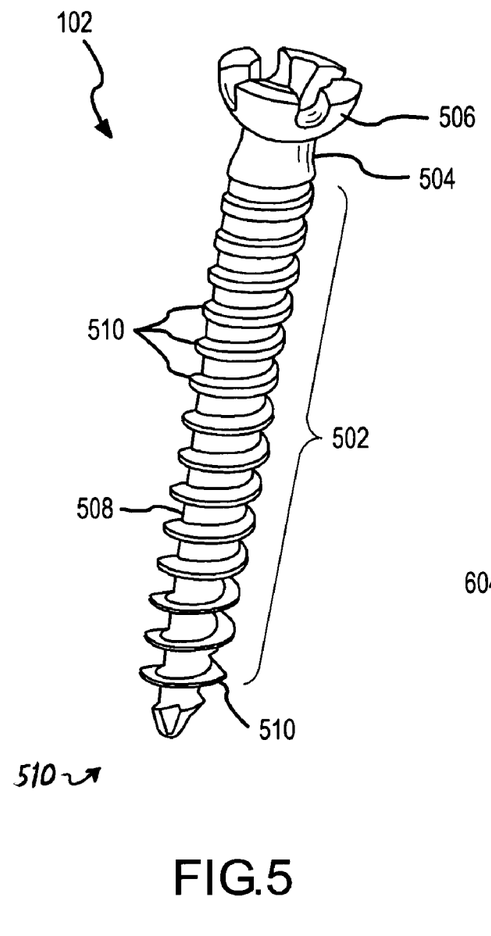
FIG. 5 shows a perspective view of a bone screw associated with an embodiment of the present invention shown in FIG. 1.

Bone screw 102 will now be described with reference to FIGS. 5 and 6. Bone screw 102 has a threaded portion 502, a transition portion 504, and a head portion 506. Threaded portion 502 can use any conventional thread, but as shown, threaded portion 502 has a shaft 508 and threads 510 machined such that shaft 508 has an increasing diameter from the tip 512 to transition portion 504. Further, threads 510 become relatively thicker towards transition portion 504. Designing threaded portion 502 in this fashion increases the frictional engagement of bone screw 102 in bone and generally increases the screw strength.

Transition portion 504 comprises the portion of bone screw 102 between threaded portion 502 and head portion 506. Transition portion 504 could be integrated into threaded portion 502. Transition portion 504 may be straight, curved, bowed, flared, or the like to transition threaded portion 502 to head portion 506.

Figure 6:
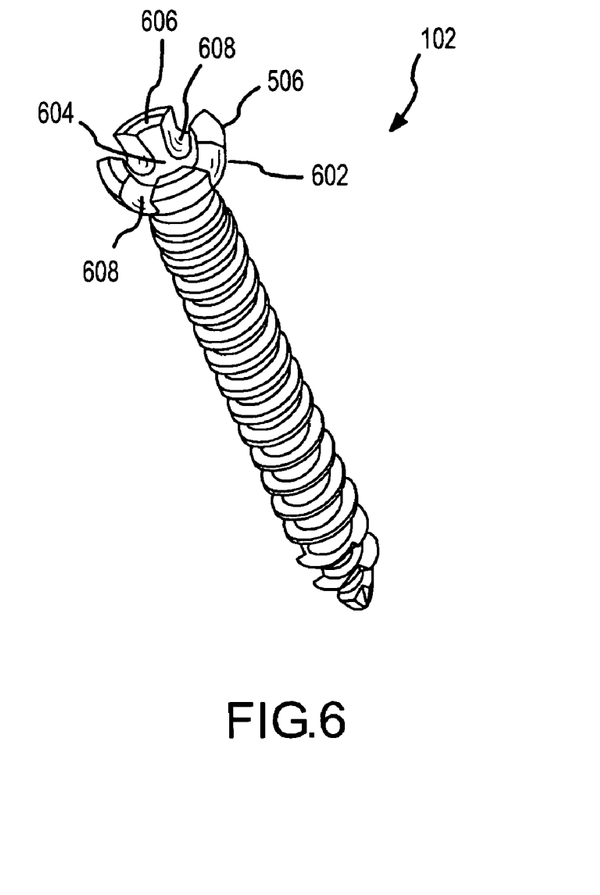
FIG. 6 shows another perspective view of the bone screw of FIG. 5.

FIG. 6 shows head 506 of screw 102 in more detail. Head 506 has a housing engaging surface 602, an insert engaging surface 604, a top edge 606, and at least one third mating surface 608, which in this case comprises a plurality of grooves. Insert engaging surface 604 has a shape corresponding to the insert, as is explained further below. Third mating surface 608 is designed to allow a surgeon to thread screw 102 into bone using a driver.

Housing engaging surface 602 has a shape corresponding to screw head seating surface 412. As shown, screw head seating surface 412 is convex in shape to mate with the concave shaped housing engaging surface 602. Housing engaging surface 602 can rotate relative to screw head seating surface 412. If designed as protrusions, upper lip 414 and lower lip 416 may provide limits on the rotation or angle of screw 102 relative to housing 104.

Figure 7:
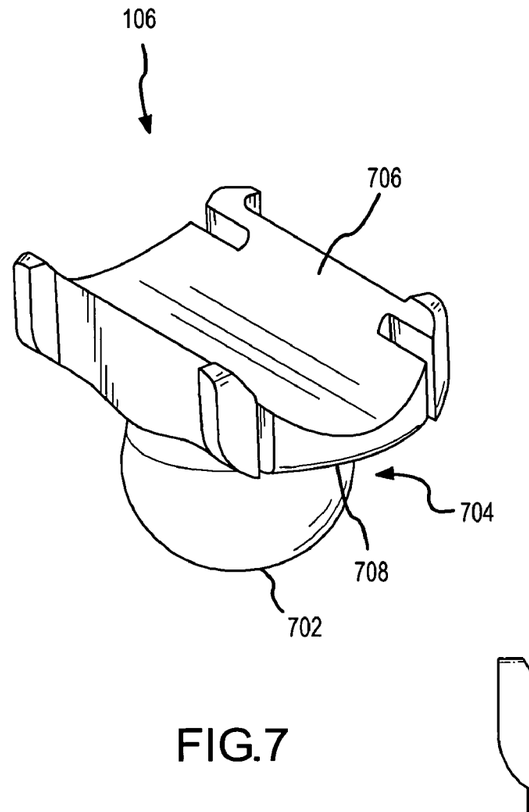
FIG. 7 shows a perspective view of an insert associated with an embodiment of the present invention shown in FIG. 1.
Figure 8:
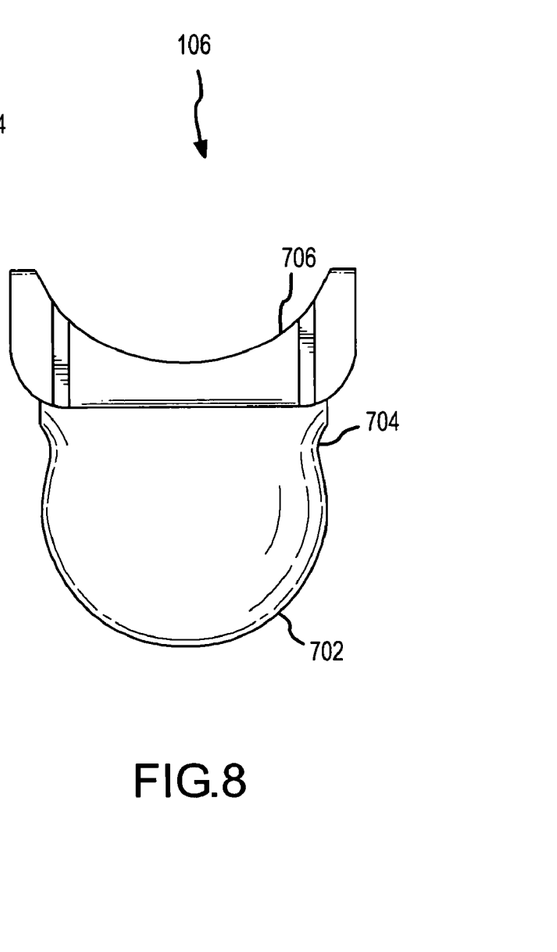
FIG. 8 shows a cross-sectional view of the insert of FIG. 7.

Insert 106 will now be described with reference to FIGS. 7, 8, and 9. Insert 106 comprises a screw head engaging surface 702, a transition section 704, and an elongated rod rest 706. Screw head engaging surface 702 has a shape that corresponds to insert engaging surface 604. In this case, insert engaging surface 604 is concave shaped to mate with convexly shaped screw head engaging surface 702. The corresponding surfaces 604 and 702 allow polyaxial orientation of screw 102 relative to insert 106. Moreover, insert 106 and housing 104 remain aligned or substantially aligned. Transition section 704 is a provides a transition between screw head engaging surface 702 and elongated rod rest 706. Transition section 704 is somewhat narrower than the largest diameter of surface 702 to increase the rotational engagement between the screw and insert.

Elongated rod rest 706 traverses housing 104 between opposing slots 308. Elongated rod rest 706 has a bottom surface 708 shaped to fit in insert seating surface 408. Elongated rod rest 706 is shaped to receive rod 108. Optionally, rod rest 706 may be solid as shown or substantially void as a matter of design choice; however, it is believed providing a substantially solid rest provides a more stable construct.

Figure 9:
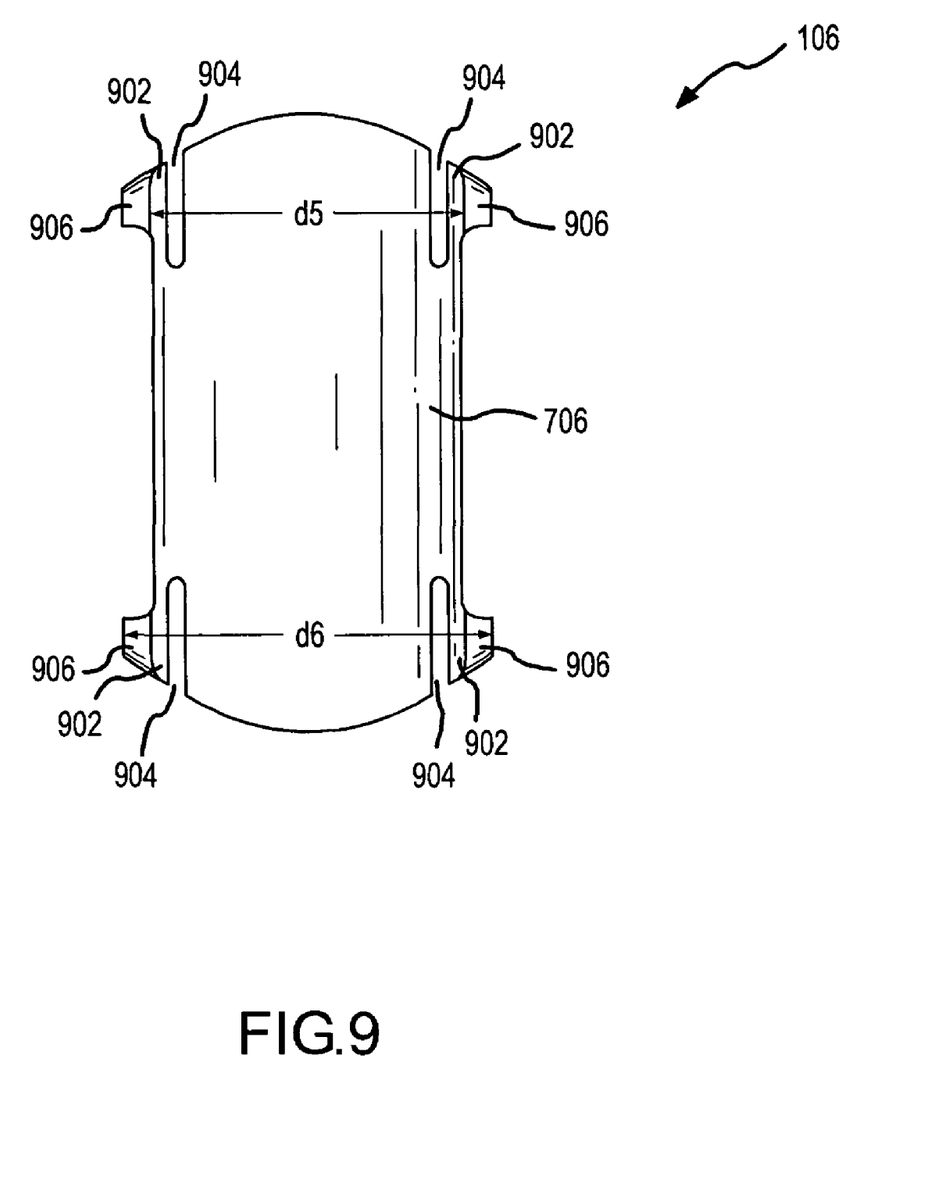
FIG. 9 shows a top elevation view of the insert of FIG. 7.

Referring now to FIG. 9, a top elevation view of insert 106 is provided. As shown, elongated rod rest 706 has a plurality of tabs 902 formed by slots 904. Each tab 902 has a protrusion 906. Insert 106 is placed in housing 104 by compressing tabs 902 as allowed by slots 904 toward rest 706. When compressed, protrusions 906 are a distance d5 apart, where d5 is less than W1. When compressed, insert 106 can be fitted into through hole 312 of housing 106 until screw head engaging surface 702 rests on insert engaging surface 604. Once surface 702 and surface 604 are in place, the compression on tabs 902 is released and tabs 902 return to the uncompressed state such that protrusion 906 are a distance d6, where d6 is greater than d5 and W1. Protrusions 906 engage groove 410 (FIG. 4) to lock and stabilize insert 106 in housing 104.

Figure 10:
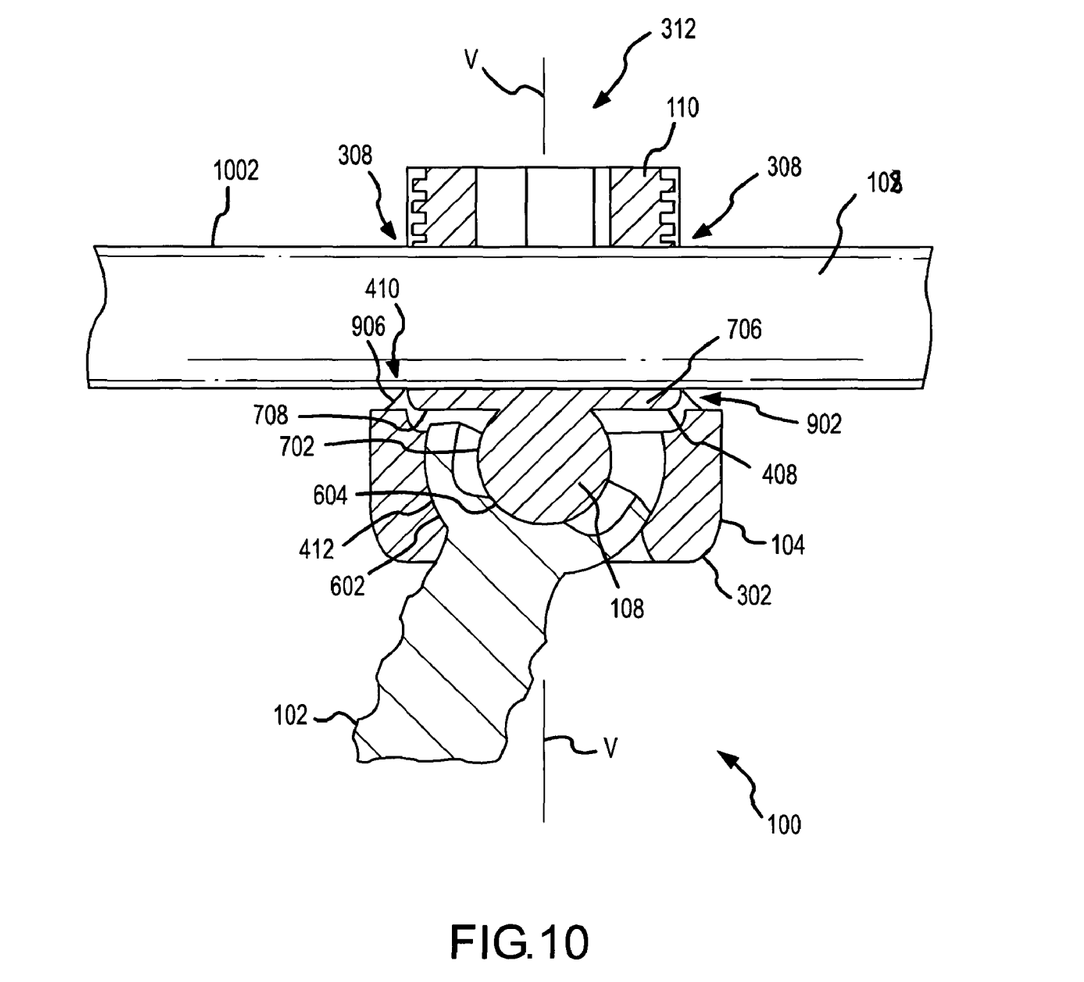
FIG. 10 shows a detailed cross-sectional view of the construct shown in FIG. 2.

With reference to FIG. 10, placement of system 100 will be explained. First, screw 102 is inserted through through hole 312. Screw 102 is partially driven into bone, not specifically shown in the FIG, until bone facing surface 302 seats on the bone and housing engaging surface 602 engages screw head seating surface 412. Screw 102 may be angled relative to a vertical axis V of housing 104. Also, housing is aligned such that opposing slots 308 will align with rod 108. Screw 102 also may have a polyaxial orientation relative to insert 106. Rod 108 is placed on elongated rod rest 706 and setscrew 110 is threaded into through hole 312 until setscrew 110 contacts rod 108 placing the construct under sufficient compression to stabilize and lock the device in place. As shown, threads 406 substantially terminate at a top surface 1002 of rod 102. This allows sufficient thread to provide the necessary force without providing unnecessary thread. Thread 406 could stop substantially at or above top surface 1002, but in that case, setscrew 110 should be designed with a boss. The thread design reduces the spreading of the housing 104 when the setscrew is tightened to rod 108.

The above construct is very stable in part because of the surface-to-surface contacts provided by various engaging surface. Further stability is provided in some instances by the insert coupling with a groove in the housing an providing a surface-to-surface contact between the rod and insert.

While the invention has been particularly shown and described with reference to an embodiment thereof, it will be understood by those skilled in the art that various other changes in the form and details may be made without departing from the spirit and scope of the invention.

We claim
1. A system useful in spinal corrective procedures, the system comprising:
a bone screw;
a housing;
an insert;
an elongated rod;
a setscrew;
the bone screw comprising;
    a threaded portion, and
    a head comprising a housing engaging surface and an insert engaging surface; the housing comprising;
    a bone facing surface and a top edge with at least one sidewall extending therebetween;
    a through hole extending from the top edge to the bone facing surface;
    at least a pair of opposing slots proximate the top edge;
    a screw head seating surface, the screw head seating surface shaped to cooperatively engage the housing engaging surface to allow polyaxial orientation of the bone screw relative to a vertical axis of the housing; and an inner surface comprising a groove, the through hole defining a first transverse inside dimension nearer the top edge and the groove defining a second transverse inside dimension smaller than the first transverse dimension further from the top edge;
the insert comprising:
    a screw head engaging surface, the screw head engaging surface shaped to cooperatively engage the insert engaging surface to allow polyaxial orientation of the bone screw relative to a vertical axis of the housing; a rod rest shaped to seat a portion of the elongated rod, the rod rest aligning with the pair of opposing slots and a narrowed transition portion coupling the screw head engaging surface and the rod rest, the transition portion having narrower cross-sectional width than a maximum width of the screw head engaging surface, and the transition portion having narrower cross-sectional width than a maximum width of the rod rest shape, so as to allow the pedicle screw and the insert additional rotation; and
    at least one protrusion resiliently deflectable from a first position to a second position, the insert being passable axially into the through hole through the first traverse dimension and into the groove with the protrusion in the first position, and the insert being retained in the groove with the protrusion in the second position;
wherein the elongated rod is seatable on the rod rest and securable by the setscrew.

2. The system of claim 1, wherein the bone screw comprises a shaft having threads, the shaft expanding radially outward from the tip to a transition between a threaded portion and a head portion.

3. The system of claim 1, wherein the housing engaging surface comprises a convexly shaped surface.

4. The system of claim 3, wherein the insert engaging surface comprises a concavely shaped surface.

5. The system of claim 4, wherein the screw head engaging surface comprises a convexly shaped surface corresponding to the concavely shaped insert engaging surface.

6. The system of claim 3, wherein the screw head seating surface comprises a concavely shaped surface corresponding to the convexly shaped housing engaging surface.

7. The system of claim 1, wherein the bone screw further comprises a tool-mating surface so a surgeon can thread the bone screw in bone.

8. The system of claim 1, wherein the housing comprises:
a rod receiving section and a screw receiving section; and
the screw receiving section comprising an upper lip and a lower lip about the screw head seating surface.

9. The system of claim 8, wherein the upper lip and the lower lip the rotation of the housing engaging surface.

10. The system of claim 8, wherein the bone facing surface connects to the at least one sidewall by a beveled section.

11. The system of claim 8, wherein an inner surface flares radially outward from the lower lip to the bone facing surface.

12. The system of claim 1, wherein the at least one protrusion comprises a portion of a tab coupled to the rod rest and separated from the rod rest by a slot, and the tab is subjectable to a compressive force that allows the insert to be inserted into the housing when the compressive force is applied and the protrusion engages the groove when the compressive force is removed.

13. The system according to claim 1, wherein the pair of opposing slots terminate in an insert seating surface having a shape corresponding to a bottom of the rod rest and the rod rest traverses the housing and extends into the pair of opposing slots above the insert seating surface.

14. The system according to claim 1, further comprising the setscrew having first threads; and
wherein the housing comprises an inner surface having second threads proximate the top edge corresponding to the first threads such that the setscrew can be threaded in the through hole and provide a compressive force on the elongated rod.

15. The system according to claim 14, wherein the first threads extend from the top edge to substantially about a top of the elongated rod.

16. The system according to claim 14, wherein the first threads extend from the top edge to substantially above a top of the elongated rod.

17. The system according to claim 1, wherein:
the bone screw comprises a plurality of bone screws;
the housing comprises a plurality of housings, wherein the plurality of housings corresponds to the plurality of bone screws;
the insert comprises a plurality of inserts, wherein the plurality of inserts corresponds to the plurality of housings;
the setscrew comprises a plurality of setscrews, wherein the plurality of setscrews corresponds to the plurality of housings; and
the elongated rod comprises at least one elongated rod that traverses a plurality of said plurality of housings.

18. An implant useful in connecting a spinal correction rod to a vertebral body, the implant comprising:
a pedicle screw;
an anchor;
an insert; and
a compressive member, wherein
the pedicle screw comprises a thread portion and a head portion, the head portion comprises an anchor seating surface and an insert seating surface;
the anchor comprises a bone facing surface, a pedicle screw seating surface, a top edge, a through hole, a pair of opposed slots, and a groove; and
the insert comprises a head seating surface, a rod rest, and a narrowed transition portion coupling the screw head engaging surface and the rod rest, the transition portion having narrower cross-sectional width than a maximum width of the screw head engaging surface, and the transition portion having narrower cross-sectional width than a maximum width of the rod rest shape, so as to allow the pedicle screw and the insert additional rotation, wherein the insert releasably couples to the groove, the insert has at least one compressive tab sized to fit the groove when in the uncompressed state, wherein
the pedicle screw anchor seating surface engages the pedicle screw seating surface such that the thread portion extends beyond the bone facing surface and is capable of polyaxial orientation;
the head seating surface engages the insert seating surface and is capable of polyaxial orientation; and
the compressive member couples to the anchor to provide compressive force to the implant.

19. The implant of claim 18, wherein
the anchor seating surface comprises a convex shape;
the insert seating surface comprises a concave shape;
the pedicle screw seating surface comprises a concave shape to allow polyaxial orientation between the anchor and the pedicle screw; and
the head seating surface comprise a convex shape to allow polyaxial orientation between the pedicle screw and the insert.

20. The implant of claim 19, wherein the pedicle screw seating surface comprises an upper lip and a lower lip.

21. The implant of claim 20, wherein the upper lip and the lower lip provide limits on the rotation of the pedicle screw relative to the anchor.

22. The implant of claim 18, wherein the the head seating surface comprises more than half a spherical shape such that the transition portion is narrower than the diameter of the spherical shape allowing the pedicle screw and the insert additional rotation.

23. The implant of claim 18, wherein the anchor comprises first threads extending from the top edge toward the bone facing surface along the through hole and the compressive member comprises a setscrew having second threads corresponding to the first threads.

24. The implant of claim 23, wherein the first threads extend substantially to a top surface of a rod.

25. The implant of claim 23, wherein the first threads extend to a point substantially above a top surface of a rod.

26. An insert useful in a housing capable of coupling spinal rods to vertebral bodies, the insert comprising:
a rod rest having an outer edge and a bottom surface opposite the rod rest;
a bone screw engaging surface coupled to the rod rest including a convex protrusion cooperatively engageable with a bone screw to allow polyaxial orientation of the bone screw relative to the insert, the convex protrusion having a first traverse dimension in a first plane substantially parallel to the rod rest;
a narrowed transition portion connecting the bone screw engaging surface and the rod rest, the narrowed transition portion comprising a second transverse dimension smaller than the first transverse dimension in a second plane substantially parallel to the first plane to define a necked region between the convex portion of the bone screw engaging surface and the rod rest, and the second transverse dimension in the second plane of the narrowed transition portion having narrower cross-sectional width than a maximum width of the rod rest; and
at least one compressible portion attached to the outer edge of the rod rest;
the at least one compressible portion being movable between a compressed state and an uncompressed state such that when in the compressed state the insert is receivable in an anchor and in the uncompressed state the insert is locked to a groove in the anchor.

27. The insert of claim 26, wherein the at least one compressible portion comprises at least one protrusion.

28. The insert of claim 27, wherein the at least one protrusion is attached to a top connected to the outer edge and separated from the rod rest by a slot.

29. The inset of claim 28, wherein the at least one protrusion comprises a plurality of protrusions.

30. The insert of claim 29, wherein the plurality of protrusions comprises four protrusions coupled to each corner of the rod rest.

31. the insert of claim 26, wherein the bone screw engaging surface comprises a semi-spherical shape.

32. The insert of claim 26, wherein the rod rest comprises a shape to cooperatively engage a spinal rod.

33. The insert of claim 26, wherein the bottom surface comprise a shape to cooperatively engage a seating surface in a pair of opposed slots in the anchor.

34. An insert for a construct to couple at least one spinal rod to vertebral bodies, the insert comprising:
a rod rest having an outer edge and a bottom surface opposite the rod rest;
a bone screw engaging surface coupled to the rod rest including a convex protrusion cooperatively engageable with a bone screw to allow polyaxial orientation of the bone screw relative to the insert, the convex protrusion having a first transverse dimension in a first plane substantially parallel to the rod rest;
a narrowed transition portion connecting the bone screw engaging surface and the rod rest, the narrowed transition portion comprising a second transverse dimension in a second plane substantially parallel to the first plane smaller than the first transverse dimension to define a necked region between the convex portion of the bone screw engaging surface and the rod rest, and the second transverse dimension in the second plane of the narrowed transition portion having narrower cross-sectional width than a maximum width of the rod rest; and at least one portion attached to the outer edge of the rod rest to abut a channel in an anchor to lock the insert in the construct; and the rod rest having a rod engaging surface with a shape to provide a surface-to-surface contact between the rod rest and a rod.

35. The insert of claim 34, wherein the rod rest further comprises a bottom surface with a shape to provide a surface-to-surface contact between the rod rest and a seating surface of a pair of opposed slots in a housing.

36. The insert of claim 34, wherein at least one portion comprises at least one compressible portion.

37. An implant useful in connecting a spinal correction rod to a vertebral body, the implant comprising:
   a pedicle screw;
   an anchor; and
   an insert; wherein the pedicle screw comprises a thread portion and a head portion, the head portion comprises an anchor seating surface and an insert seating surface;

the anchor comprises a bone facing surface, a pedicle screw seating surface, a top edge, a through hole, and a pair of opposed slots; and the inset comprises a rod rest, a pedicle screw head seating surface, and a transition portion between the rod rest and the head seating surface, the rod rest has a first transverse dimension in a first plane, the head seating surface includes a convex protrusion having a second transverse dimension in a second plane substantially parallel to the first plane, the transition portion couples the head seating portion to the rod rest, the transition portion comprises a third transverse dimension smaller than the first and second transverse dimensions in a third plane substantially parallel to the first and second planes to define a necked region between the convex portion and the rod rest, wherein the pedicle screw anchor seating surface engages the pedicle screw seating surface and the head seating surface engages the insert seating surface such that the pedicle screw and anchor are capable of relative polyaxial orientation.

* * * * *